United States Patent [19]

Grove

[11] 4,326,032

[45] Apr. 20, 1982

[54] PROCESS FOR THE PRODUCTION OF ORGANIC FUEL

[76] Inventor: Leslie H. Grove, 707 E. Hoyt Ave., St. Paul, Minn. 55106

[21] Appl. No.: 189,205

[22] Filed: Sep. 22, 1980

Related U.S. Application Data

[63] Continuation-in-part of Ser. No. 68,209, Aug. 20, 1979, abandoned, which is a continuation-in-part of Ser. No. 922,748, Jul., 1978, abandoned.

[51] Int. Cl.$^3$ .................. C12P 7/08; C12R 1/145
[52] U.S. Cl. ................... 435/148; 435/842; 435/163
[58] Field of Search .............. 435/147, 148, 160, 161, 435/163, 842

[56] References Cited

U.S. PATENT DOCUMENTS

| | | | |
|---|---|---|---|
| 1,927,814 | 9/1933 | Legg | 435/160 X |
| 1,928,379 | 9/1933 | Hutchinson | 435/160 X |
| 2,182,989 | 12/1939 | Jean | 435/160 X |
| 3,711,392 | 1/1973 | Metzger | 435/165 X |
| 3,812,012 | 5/1974 | Buschmann et al. | 435/252 X |
| 4,094,742 | 6/1978 | Bellamy | 435/165 X |

Primary Examiner—Robert A. Yoncoskie
Attorney, Agent, or Firm—Merchant, Gould, Smith, Edell, Welter & Schmidt

[57] ABSTRACT

In the disclosed cellulase-catalyzed fermentation process for converting a cellulose- or hemicellulose-containing starting material to an organic fuel, the fermentation medium contains an efficient combination of Clostridium organisms or their enzymes. One preferred combination of organisms includes *Cl. cellobioparum* and *Cl. acetobutylicum*. Conversion of the cellulose to a liquid hydrocarbon oxidate proceeds in good yield with relativey minimal carboxylic acid production. The non-distillable residue is suitable for use as a fertilizer.

13 Claims, No Drawings

PROCESS FOR THE PRODUCTION OF ORGANIC FUEL

This application is a continuation-in-part of my copending application Ser. No. 68,209, filed Aug. 20, 1979, now abandoned, which in turn is a continuation-in-part of my application Ser. No. 922,748, filed July 7, 1978, and now abandoned.

BACKGROUND OF THE PRIOR ART

In recent years, there has been an upsurge of interest in so-called renewable energy resources, particularly carbohydrates. Carbohydrates can be converted to liquid organic fuels in a number of different ways. For example, simple sugars have been fermented to produce ethyl alcohol since ancient times. If liquid organic fuels obtained from carbohydrates are to be economically competitive with other energy sources, however, it is likely that starting materials for the fermentation or other microbiologically or enzymatically catalyzed syntheses will have to be selected from more complex carbohydrates or carbohydrate-containing materials, particularly materials of a cellulosic nature.

Enzymes and microorganisms capable of breaking down cellulose and hemicelluloses into mono- and oligosaccharides are known. In some instances, the same microorganism culture which breaks down the cellulose will ferment the simple sugar intermediates, thereby providing an essentially one-step conversion of cellulose to liquid organic solvents or fuels. (In actuality, of course, enzymatically or microbiologically catalyzed hydrolysis of cellulose and fermentation of the resulting simple sugars to alcohols, ketones, and the like is an extremely complex series of reactions involving many intermediates, but some of these intermediates or theoretically postulated intermediates, e.g. glyceraldehyde have only a short-term existence and do not show up in the ultimately obtained fermentation products.)

The scientific literature dealing with the utilization of cellulosic materials by microorganisms is very large. According to one study, cellulose-decomposing bacteria can be divided into three groups: (a) aerobic, (b) anaerobic, and (c) thermophilic. Very few aerobic bacteria have been used successfully for the purpose of deriving fuels or solvents from a cellulosic raw material. According to Porter, *Bacterial Chemistry and Physiology*, Wiley and Sons, Inc., New York, N.Y., 1946, page 822, "Aerobic bacteria and fungi usually bring about complete destruction of cellulose, without leaving much in the form of intermediate products; hence they have little to offer for the production of industrially valuable products." A disadvantage with thermophilic bacteria is that they tend to be inefficient or even ineffective at normal ambient or modestly elevated temperatures. In short, the use of thermophilic bacteria for decomposition of cellulose actually involves a significant energy input beyond the nutrients or nutrient sources which all microorganisms utilize for energy. Accordingly, anaerobic bacteria are typically the organisms of choice in microbiological processes for decomposing cellulose. The use of anaerobic organisms, however, has its own set of problems.

First, many anaerobic organisms have minimal aerotolerance. That is, not only are these organisms unable to make use of atmospheric oxygen as a hydrogen acceptor, they are also highly sensitive to the presence of oxygen and may even be poisoned by it. In a large industrial operation, it is generally possible to maintain strict anaerobic conditions to protect against this lack of aerotolerance. However, maintaining these conditions may be expensive and difficult, even in these large operations. Fermentation tanks typically must be purged with inert gases and sealed off from the atmosphere. The carbon dioxide generated during fermentation typically is vented through one-way valves or the like.

Second, not all cellulose-decomposing anaerobes are capable of converting the starting material to liquid organic fuels and solvents in accordance with the "one-step" procedure described previously. Typically, the action of the organism is cellulolytic in nature, the resulting hydrolyzate being a monosaccharide such as glucose, a disaccharide such as cellobiose, or the like. A further microbiological system has to be introduced into the fermentation process in order to convert the sugars into aldehydes, ketones, alcohols, and other desired fuels and solvents.

Third, not all anaerobic bacteria have sufficient nitrogen-fixing capabilities to provide a non-distillable residue which has utility as a fertilizer.

Fourth, careful control over temperature and pH conditions may be required to insure maximum efficiency. Excessively low or high temperatures or pH's may either inactivate or kill the organisms.

Fifth, the very specificity of the microorganism or its enzymes (oftentimes an advantage in some contexts) may be a disadvantage when the nature and quality of the raw material is poorly controlled. For example, if the raw material were a mixture of agricultural wastes, waste paper, municipal sewage or garbage, or other materials equally variable in content, it is possible that not all glycosides will be broken down into simple sugars. Specificity in the ultimate products of the fermentation can also be a disadvantage if the fermentation product is essentially ethyl alcohol or a mixture containing ethyl alcohol which is easily distilled to provide the pure water-alcohol azeotrope (190 proof alcohol). This water-alcohol azeotrope is subject to heavy taxation unless it is denatured in accordance with one of the accepted denaturing formulas. Even the production and sale of denatured alcohol entails involvement in a complicated regulatory scheme which may be burdensome for the solvent or fuel manufacturer, particularly when the manufacture is being carried out on a small scale or low-volume basis.

Finally, and perhaps most important, even if the cellulose can be converted to simple liquid organic chemicals in accordance with the aforementioned "one-step" approach, the resulting products may be mixtures with little industrial utility. In the field of solvents, there is ordinarily a much greater demand for single-solvent systems which can be blended to suit the particular application. A mixture of, say, 1-butanol and acetic acid in some ratio which is arbitrarily determined by the microbiological system might be totally unsuited to most solvent applications, and separation of the alcohol from the acid might be uneconomical. In the field of fuels, the chemical identity and ratios of the components of the fuel may be less critical, provided that the overall heat of combustion is substantial, e.g. above 4 Kg-cal/g. Even in the case of relatively sensitive use of fuels (e.g. motor fuels), a mixture of various oxo- or oxy-aliphatics (including cyclo-aliphatics) can perform very adequately, provided certain volatility and anti-knock requirements are met. (Ever since the internal combustion engine was invented, oxo- and oxy-aliphatics have been used successfully—the essentially pure hydrocarbon character of modern gasoline results from the ready availability of hydrocarbon fuels rather than the inability to adapt alcohols, ketones, etc. to this use.)

That is not to say that any oxo- or oxy-aliphatic mixture obtained by fermentation of cellulose can be used as a fuel. Major fermentation products may be objectionable because they are corrosive, lacking in anti-knock properties, too low in volatility, unpleasant in odor, or too low in energy content, e.g. below about 4 Kg-cal/g. From the standpoint of lack of volatility, higher molecular weight aliphatic carboxylic acids, non-polyhydric alcohols, and mixed functional group compounds (e.g. alpha-hydroxy carboxylic acids)—all known to be products of various anaerobic fermentations—are perhaps the primary offenders. Some of these compounds are solids at room temperature. Others boil at temperatures above 200° C., even though they may be liquids under normal ambient conditions. In addition, the $C_3$-$C_6$ aliphatic carboxylic acids can be highly objectionable because of odor and corrosion problems.

The lower carboxylic acids, particularly formic acetic acids are objectionable for a variety of reasons. Their odors are strong, their boiling points are relatively high compared to other $C_1$ and $C_2$ compounds (such as the alcohols and carbonyl compounds), they are corrosive, and their energy content is well below, for example, ethyl alcohol. Yet many of the cellulolytic anaerobes produce significant amounts of carboxylic acids. Indeed, lower carboxylic acid and alpha-hydroxy carboxylic acid production are common applications of anaerobic fermentation technology.

SUMMARY OF THE INVENTION

It has now been found that a deliberate combination of microorganisms of the genus Clostridium (or the enzymes produced thereby) can be utilized to convert cellulose directly to a liquid organic fuel or relatively high energy (e.g. above 4 KG-cal/g when anhydrous). It has been found that at least two Clostridium species (or their enzymes) should be used in combination to achieve this result. Both species are preferably somewhat aerotolerant, and both should be carbohydrase-producing. One of the two species should be capable of producing cellulase, and other species preferably produces cellobiase, glucosidase, and/or glucase. Typical of such combinations would be *Cl. cellobioparum* with a saccharase-producing organism such as *Cl. acetobutylicum*. The enzymes produced by these organisms can be used without associated live cellular material, with some advantages, particularly with respect to sensitivity toward air, temperature changes, pH shifts, and the like. It is well known in the art of microbiology that, whenever two cultures are combined with the objective of adding together their functions, the results are essentially empirical and must typically be determined by experiment. It can often happen that microbiological cultures work in opposition to each other rather than in cooperation. However, not only do the Clostridium species used in this invention cooperate, the resulting suppression of carboxylic acid formation is believed to be truly suprising.

The deliberate combination of Clostridium organisms (or their enzymes) is effective for a variety of substrates, including commonly occurring cellulosic materials (agricultural wastes, municipal sewage, waste paper, and other inexpensive sources of cellulose and hemicelluloses). Although ratios of the deliberately combined organism populations (or enzyme activity) used in this invention can range from about 1:9 to 9:1 with respect to the two Clostridium species, it is preferred to maximize alcohol/ketone production and minimize carboxylic acid production, which objective appears to be obtained most effectively with at least 40% (by weight or activity or population) of the cellulase system or cellulase-producing organism, more preferably 50–80%. The preferred fermentation agent or fermenting organisms have at least some aerotolerance. The nitrogen-fixing capabilities of the preferred combinations of microorganisms are adequate to provide a non-volatile residue with properties making it useful as a fertilizer. Fermentation can proceed under normal ambient or moderately elevated temperatures, e.g. 30°–40° C. The preferred pH in the fermentation zone ranges from about 3 to about 7, more preferably at least 3.8, the optimum pH range being 5.8–6.4. The fuel obtained from a cellulose decomposition process of this invention is non-potable, relatively high energy, volatile (typically boiling within the range of 20° to 200° C.), and typically high in antiknock properties. High yields of this fuel are obtained in an efficient manner. Indeed, the efficiencies and the economies of the process of this invention are sufficient to permit small scale, low volume production—as low as a few gallons per week for the small farmer.

To sum up the key aspects of the process:

(a) Water, a cellulose- or hemicellulose-containing particulate mass, and a fermentation agent of this invention are blended to form a fermentation medium. The fermentation agent comprises the combination of Clostridium organisms described previously (or their enzymes).

(b) The particulate mass is permitted to ferment until fermentation products are produced.

(c) The resulting non-potable hydrocarbon oxidate fuel is then recovered from the fermentation medium by conventional means. The most commonly used conventional means is distillation; however, it is also known to utilize the principles of fractional crystallization, solvent extraction with gasoline (see U.S. Pat. No. 3,711,392 [Metzger], issued Jan. 16, 1973, column 15, line 5 et seq), and any other practical means for separating water from lower aliphatic fuels such as aldehydes, ketones, and alcohols.

Although the process of this invention most likely goes through at least two distinct stages and may involve a number of intermediates, changing of the fermentation medium is not required and can be undesirable, particularly in small scale operations. The most probable first stage of the reaction involves swelling of the particles with water for a period of time typically lasting about 12 to 48 hours and can proceed at normal ambient to moderately elevated temperatures. The most probable second stage of the process which typically lasts another 12 to 48 hours apparently involves both hydrolysis of cellulose and of oligosaccharides, along with fermentation of simple sugars to $C_1$-$C_6$ (more typically $C_1$-$C_4$ or $C_5$) oxo- or oxyaliphatics such as alcohols, aldehydes, and ketones.

DETAILED DESCRIPTION

The exact nature of the cellulosic starting material used in the process of this invention is not critical. Virtually any organic material containing cellulose or hemicellulose can be used. Representative materials include agricultural wastes (cornstalks, corn cobs, potatoes, grassy plants, straw, weeds, etc.), sewage, manner, waste paper, wood waste, pulp (sulphite pulp, kraft pulp, soda pulp, etc.), food wastes, waste liquors from pulp mills, and the like. Thus, the starting material can contain non-cellulosic materials such as lignin, pectin, protopectin, proteins and other polypeptides, and various types of glycosides. The glycosides can even contribute to the yield of useful products. The proteins and other nitrogen-containing compounds can contribute to the value of the residue as fertilizer. Another particularly useful ingredient in the raw material is starch. Starch is generally much easier to hydrolyze than cellulose, and any of a variety of amylase enzymes or amylase-secreting organisms will typically break the starch down into single glucose units which serve as an excellent substrate for fermentation.

Despite the inherent utility of these non-cellulosic materials which may be included with the cellulose, it is generally preferred to expose the cellulose to enzymatic action. For example, it is desirable to strip away lignin or pectinaceous sheaves or coverings which may impede hydrolysis of cellulose. Cellulose can be better exposed to enzymatic hydrolysis through bacterial action (e.g. by treatment of the cellulosic raw material with a suitable Bacillus culture), but the preferred approach is mechanical in nature, e.g. pulverizing the starting material to provide a particulate mass which will pass a 50 U.S. mesh screen, more preferably a 100 mesh screen. Conventional grinders, homogenizers, and the like are suitable for this purpose. Grinding or shredding of the raw material apparently helps to liberate some of the cellulose and speed up the hydrolysis.

The resulting particulate mass is blended with water to provide a slurry-like mass which is preferably pumpable. Pumping of this slurry-like mass becomes extremely difficult as the solids level approaches 50% by weight. On the other hand, a practical, high level of solids content is desirable to facilitate separation of the fermentation products from water at or near the conclusion of the process. From 5 to 10% solids is a typical practical lower limit, but, theoretically at least, the slurry could be far more dilute. The optimum solids level appears to be somewhere within the range of 15 to 35% by weight. Substantially the balance of the fermentation medium (with the exception of the fermentation agent) can be ordinary tap water. Distilled or deionized water can be used but is by no means essential to the effectiveness of any hydroysis or fermentation which occurs in the fermentation medium.

The fermentation agent comprises the aforementioned Clostridium organisms (in combination) or their enzymes. Although this invention is not bound by any theory, it is presently believed that the enzymes provided by preferred fermentation agents of this invention include a variety of carbohydrases including cellulase and one or more saccharases. In addition, proteases, amylases, and lipases are believed to be present; the proteases and lipases are believed to make a contribution to the liberation of the cellulose from outer coverings of non-cellulosic materials. Other carbohydrases believed to be present include cellobiase and/or glucosidase and/or glucase. All of these enzymes can be utilized without associated live cellular material in accordance with principles known in the art. For example, it is known that enzymes can be obtained from natural sources in more or less pure form. The isolation of enzymes is relatively simple when the organism or natural source produces (e.g. secretes) the enzyme extracellularly. Techniques are also known for isolating intracellularly produced enzymes, e.g. ultrasonic destruction of the cellular material followed by various chemical and/or physical separation steps.

Among the known methods of obtaining concentrated enzyme preparations is the so-called adsorption method, introduced by early workers and further improved by Willstaetter et al. It is based on the separation of the enzyme from extraneous matter by adsorption on a suitable colloid, such as kaolin, certain aluminum hydroxides, or other gels, and the subsequent freeing or elution of enzyme from the adsorbent. This method of purification is based on the greater affinities of the adsorbent for the enzyme than for the impurities; by repeating the procedure several times a concentration of the enzyme is obtained. Another technique involves dissolving the enzymes in a suitable solvent and precipitating them with various reagents or by electrophoretic methods. Changes in pH and temperature, dialysis, and other measures are often employed to remove impurities or concentrate or crystallize the enzyme. Additional methods are known. For example, if the association between the enzyme and the cellular material is not detrimental to enzyme activity, a microbiological culture can simply be killed, dried, and ground into a powder—the powder being a reasonably potent source of the enzyme. See U.S. Pat. No. 3,824,184 (Hatcher et al.), issued July 16, 1974, which describes a very simple technique for isolating the enzyme levan hydrolase. Finally, chemical synthesis techniques can be used to link amino acids or polypeptides or purine or pyrimidine bases or ribose units or the like into enzyme-like structures.

In the case of the organism *Clostridium cellobioparum*, the preferred cellulose-decomposing organism of this invention, it has been reported that profuse growth occurs in the presence of fermentable carbohydrate. Such profuse growth has been observed in practice. Accordingly, attainment of enzyme concentrates from a fermentation broth or production medium appears to be economically practical. Similar profuse growth has been obtained with other Clostridia.

Many Clostridia have poor aerotolerance. Ideally, these organisms are grown under strictly anaerobic conditions at a pH ranging from 5.8 to 6.4 and at an ambient temperature of about 35°–38° C. Some improvements in aerotolerance appear to be obtained by transferring the anaerobically grown colonies to a new growth zone which is not sealed off from the atmosphere. This transfer procedure can be repeated 5 to 8 times (always under aerobic conditions) to continue the trend toward improved aerotolerance. Following this procedure, hearty cultures can be obtained, at least about 10% of which can survive aerobic conditions and produce useful fermentation products. If the enzyme concentrate preparation procedure is followed, the resulting concentrates are highly advantageous in terms of far less sensitivity to air, pH shifts, and temperature changes.

For example, there appears to be very little in the way of a spontaneous pH shift when enzyme concentrates are used to ferment the cellulosic starting material. (with the live organisms, on the other hand, there is some danger that the pH will spontaneously shift downward toward 3.0 or even lower, resulting in a fast kill rate for the organisms.) With little or no pH manipulation, the enzyme-catalyzed processes of this invention tend to remain approximately in the 5 to 7 pH range. Enzymes can be deactivated by high temperatures, e.g. above 65° C., but temperatures on the order of 40 or even 50° C. appear to have very little adverse effect. No adverse effect has presently been observed at temperatures below 45° C. Furthermore, the enzymes appear to be active at normal ambient or room temperatures, e.g. 20°–25° C., and activity at temperatures as low as 5° or 10° C. has been observed. (With live clostridia, on the other hand, the 30°–40° C. range is preferred; although some clostridia are effective at lower and higher temperatures, the greatly preferred *Cl. cellobioparum* appears to be most effective in this range.)

In addition to the carbohydrase enzymes described previously, other useful enzymes are believed to include cellobiohydrolase or cellobiase and hemicellulase. Although *Cl. cellobioparum* is the clearly preferred cellulase-producing microorganism, other closteridia are known to have cellulolytic properties. According to Porter, *Bacterial Chemistry and Physiology*, cited previously, at page 821, anaerobic bacteria said to have these properties are called *Cl. cellulosae-dissolvens*, *Cl. cellulosolvens*, and *Cl. cellulolyticum*. A thermophile that digests cellulose is *Cl. thermocellum*, which occurs in human and animal feces; however, it should be noted that fermentation products for this organism are reported to include formic, acetic, lactic, and succinic acids.

According to Bergey's Manual, *Cl. cellobioparum* is said to produce from cellulose a set of fermentation products including acetic acid. (This organism has been found in rumen contents.) Suprisingly, however, this tendency to produce acetic acid appears to be somewhat suppressed or overshadowed when the process of this invention is properly practiced.

The genus Clostridium has been divided into four groups. *Cl. cellobioparum* is included in Group III. Other preferred organisms from Group III include *Cl. sphenoides* and *Cl. indolis*, despite the poor aerotolerance of these species. These species are of interest for their ability to ferment glucose, cellobiose, and other mono- and poly-saccarides. A typical combination of organisms in accorcance with this invention (or combinations of the enzymes thereof) typically involves selection of the second clostridium species from Group I or Group II. The preferred Group I species is *Cl. butyricum*, and the preferred Group II species are *Cl. felsineum* and *acetobutylicum*. The last of these (*Cl. acetobutylicum*) is reported to have very little activity toward cellobiose, but good activity toward glucose, fructose, starch, sucrose, mannose, maltose, lactose, and other sugars of this type. Accordingly, it presently appears that *Cl. acetobutylicum* is not useful in itself in this invention, but rather in combination with other organisms such as *Cl. cellobioparum*. On the other hand, the use of *Cl. cellobioparum* by itself can result in the production of excessive amounts of acetic acid, which is not desired in the context of this invention.

As noted previously, the process of this invention can be carried out without change of fermentation medium or broth, even though the series of reactions occurring in the broth or medium appears to proceed in fairly definite stages. The primary objective in the early stages of the process is to bring the cellulosic material into maximum contact with water, swelling the material and improving the efficency of the hydrolysis which follows. The hydrolysis of cellulose and the fermentation of cellulose and simple sugars to the desired oxo or oxy aliphatic fuel is undoubtedly a multistage process in itself, although the entire series of reactions could reasonably be summed up with the single term "fermentation." Agitation of the fermentation medium is desirable but not essential. When agitation is used, it is not necessary to employ stirrers, mixers, or the like. It can be sufficient to simply pump the slurry-like medium from one tank to another, using conventional pumping equipment. Mixers, homogenizers, grinders, and the like can be placed in-line with the pumping equipment, thereby further improving the uniformity of the slurry-like mass.

As noted previously, recovery of the non-potable oxy or oxo aliphatic fuel from the fermentation products produced by the fermentation medium can be carried out by a variety of conventional means. For fuels used in simple combustion processes (and even, to some extent for motor fuels) conventional distillation and refluxing is sufficient, despite the presence of water in the distillate. If desired, the distillate can be made anhydrous by known techniques, e.g. addition of calcium oxide, hydrocarbon entrainers, or other dehydrating agents.

Enzyme-catalyzed decomposition of mono- and poly saccarides is known to produce a variety of oxygen-containing organic liquids, including cycloaliphatics (such as furfural, furfuryl alcohol, etc.), unsaturated aliphatics (such as the enol form of pyruvic acid), and saturated aliphatics, particularly the lower aliphatics (i.e. those having six carbons or less). When the cellulosic material includes lignin or other complex non-cellulosic material, some aromatics can be obtained (e.g. benzaldehyde, cinnamaldehyde, anisealdehyde, and the like). Undesired organic and inorganic products, if present, can be eliminated by techniques known in the art.

Some gases can be produced, principally carbondioxide, hydrogen, and methane.

The lower aliphatics are of primary interest with respect to liquid organic fuels. The preferred lower aliphatics are in the $C_1$ and $C_5$ range, optimally the $C_1$–$C_4$ range. Foremost among these are the carbonyl compounds (particularly aldehydes and ketones) and the monohydric alcohols such as the lower alkanols. As noted previously, $C_1$ through $C_6$ carboxylic acids (including alph-hydroxy carboxylic acids) have been reported to occur in the fermentation products, but an objective of this invention is to minimize production of these acids.

From the standpoint of motor fuel production, the most desirable alcohols and carbonyl compounds are the $C_1$–$C_4$ alcohols and acetone. The amyl alcohols are also suitable for motor fuel use, but their higher boiling points can be a disadvantage where highly volatile motor fuel is desired. The antiknock properties of methyl alcohol, ethyl alcohol, and acetone are so outstanding that these compounds can be considered to have value as antiknock additives. The "blending octane value" of methyl alcohol has been reported to be as high as approximately 130, and that of ethyl alcohol reported to be only a few numbers lower. As anhydrous organic liquids, they make outstanding additives for conventional modern gasolines, and they are also excellent motor fuels in themselves. Methanol/ethanol blends are desirable in that the ethanol component is, in effect, denatured by the methanol, which cannot be readily removed by distillation. For this reason, methanol is an accepted denaturent. Fermentation products other than ethanol and methanol have similar denaturing effects, causing the fuels produced in accordance with this invention to be non-potable.

Not only are the preferred fuels of this invention relatively free of acetic acid (e.g., less than 15%, preferably less than 5% by weight on an anhydrous basis) essentially no formic or butyric acid has been detected in these preferred fuels. This suppression of carboxylic acid formation is not presently understood. These preferred fuels boil within the range of 50°-140° C. (more preferably below 100° C.) and have a heat of combustion in excess of 4 Kg-cal/g, more typically above 5 Kg-cal/g.

The residue from the process of this invention is useful as fertilizer. More than 250 Kg of fertilizer per metric ton (1,000 Kg) of starting material can be obtained in accordance with the process. Typically, the amount of fertilizer produced is 900–1,100 lbs. per ton of cellulosic starting material (approximately 400–500 Kg per metric ton).

Although various mixtures of cellulase-producing (e.g. *Cl. cellobioparum*) and saccharase-producing (e.g. *Cl. acetobutylicum*) Clostridia organisms or their enzymes will be effective for the production of lower alcohols and ketones, alkanol/ketone production is apparently maximized and most efficient with mixtures containing at least 40% (by weight, by units of enzyme activity, by microorganism population, etc.) of the cellulase or cellulase-producing organism, more preferably a major amount of this component. When enzymes are used, ratios or percentages of the two active components of the mixture can be determined, for example, on an enzyme-activity-units-per-gram basis. When live organisms are used, organism density (number of live organisms per cubic centimeter) can be determined spectrophotometrically using a suitable wavelength (e.g. 650 nm) or by some similar method, and each component can be diluted to the desired density and blended or shipped in separate containers in pre-measured amounts and then combined before use. As the mixture or organisms or enzymes approaches 90% *Cl. acetobutylicum*, acetone becomes a more predominant product and sugar buildup can reach levels which may inhibit reaction rates. Unless a high proportion of acetone is desired, the proportion of *Cl. acetobutylicum* or other sugar-fermenting organism (or enzyme) is preferably kept below 60%, e.g. 20–50%. For a high energy, efficiently produced lower alkanol fuel from corn plant waste (stalks, cobs, etc.) of very modest acetone content, 60–70% *Cl. cellobioparum* and 30–40% *Cl. acetobutylicum* appears to be an optimum mixture.

Typical fermentation beers contain about 3–20% by weight of organic liquids (preferably 5–15%), the most typical organic liquids being ethyl alcohol, n-propyl alcohol, butyl alcohol, amyl alcohol, acetone, and, in very minor amounts, acetic acid.

Through simple manipulations of conditions well within the skill of the art, fuels made according to this invention can be shifted from the motor fuel category into fuels suitable for cooking, space heating, heating of steam boilers or hot water heaters, heating of themo elements, driving of heat-operated machines utilizing the refrigeration cycle, and a variety of other uses known to those skilled in the art.

The principle and practice of this invention is illustrated in the following Example.

EXAMPLE I

The following fermentation was carried out with no attempt to maintain strictly anaerobic conditions, using surviving cultures of *Cl. acetobutylicum* and *Cl. cellobioparum* which had been grown initially under anaerobic conditions, using boiled calf liver and cellulosic material as a growth medium and a 90:10 $N_2:CO_2$ gas purge, then transferred eight times to eight different vessels under aerobic conditions.

A sample of agricultural waste consisting essentially of cornstalks was ground up into a minus 50 U.S. mesh particulate mass and then pulverized further in a blender to minus 100 mesh. The $-100$ mesh cornstalk particles were mixed with tap water in the ratio (by weight) of 3:1 water:cornstalk to provide a 25 weight-% solids, slurry-like mass. This 25% solids medium was placed in an enclosed (but not sealed or purged) fermentation vessel. The aforementioned surviving *Cl. cellobioparum* and *Cl. acetobutylicum* cultures were added to complete the formation of the fermentation medium. The fermentation vessel was kept at normal ambient temperatures (20°-25° C.) for 24 hours and was then placed in a heated room kept at a temperature within the range of 35°-38° C. The pH of the fermentation medium in the vessel was monitored (using a conventional electrical pH meter) and kept generally within the range of 5 to 6.5. During the next 24-hour period (while the fermentation vessel was kept at 35°-38° C.), gas bubbles formed, liquids formed and rose to the tope of the medium, and particulate matter settled. The liquid mixture in the fermentation zone was analyzed using a hydrometer and found to contain slightly less than 8.5 vol.-% lower aliphatic compounds, essentially the balance of the liquid being water. On an anhydrous basis, the predominantly-occurring lower aliphatic compounds were present in generally the following ratio: 1.85:1.15:1.00 (by weight or volume) 1-propanol:ethanol:methanol. Traces of acetone, butyl alcohol, and acetic acid were detected. According to published data, this fuel (tested on an anhydrous basis) would have a heat of combustion in excess of 5.3 Kg-cal/g. The BOV (blending octane value) would be in excess of 100, for a 20% addition to 85-octane gasoline.

Similar results were also obtained with dried enzyme from the Clostridium organisms, except that the enzymes were fully effective at 21°-25° C. The pH remained stable without manipulation.

Similar results were also obtained using grass clippings and waste paper instead of cornstalks. Variable results were obtained with more highly nitrogenous starting materials such as manure. Hog manure provided alcohols, but cow manure did form a significant amount of acetic acid. A sample of municipal sewage (3% by weight solids) gave a butyl alcohol:ethyl alcohol:methyl alcohol mixture in the ratio of 1.2:2:2.6. Thus, sewage, plant (particularly leafy) materials, and non-ruminant manure all appeared to provide reliable sources of $C_1$-$C_4$ non-carboxylic oxo- or oxy-aliphatic fuels. Yields were generally good, e.g. 40 to 50 wt.-%, based on solid cellulosic starting material.

EXAMPLE II

Live *Cl. cellobioparum* and *Cl. acetobutylicum* organisms in growth media were diluted to a convenient number of organisms per cubic centimeters, as determined by a 650 nanometer-line spectrophotometer. With roughly equal populations per $cm^3$ established, volumes of diluted growth media were combined to provide a 65/35 *Cl. cellobioparum/Cl. acetobutylicum* organism population ratio. The initial growth medium contained, per liter of distilled water:

| NaCl: | 6g. |
|---|---|
| MgSO4: | 0.1 g. |
| (NH4)2SO4 | 1.0 g. |
| KH2PO4: | 0.5 g. |
| CaCl2: | 0.1 g. |
| Yeast extract: | 1.0 g. |
| Cellulose: | 5.0 g. |

The organisms were grown under anerobic conditions in previously-autoclaved, sealed containers which were purged with 90% N2/10% CO2.

The agricultural waste introduced into the fermentation vessel was again corncobs and cornstalks, ground as in Example I. The bacteria growth medium formed 4 to 6% of the fermentation tank volume. The fermentation tank was not purged with inert gases, but it was heated to 100° F. (38° C.) before the Clostridia were added.

After the fermentation was completed, the beer was concentrated to a 20% water/80% organic liquid mixture using a so-called "stripper" device supplied by Ferguson PO-W-ER Fuel, Inc. of Dunreith, Ind. The fuel sample was analyzed and found to contain 5% acetone, 11% ethyl alcohol, 14% n-butyl alcohol, 41% n-propyl alcohol, 8% n-amyl alcohol, and only 1% acetic acid, the balance being water. The heating value of this fuel was 13,412 BTU/lb or about 7.5 kg-cal/g. The octain rating of the fuel was 114, and under pressure combustion there was an 82.4% recovery from theoretical. The open flame temperature was 1460° F. (793° C.). The very high proportion of n-propyl alcohol was considered advantages.

EXAMPLE III

The procedure of Example II was repeated exactly except for the *Cl. cellobioparum/Cl. acetobutylicum* ratio, which was 50/50 instead of 65/35. This 50/50 fermentation agent produced a fuel which, concentrated to 69% organics, was found to contain

| 25% | acetone |
|---|---|
| 22% | n-butyl alcohol |
| 12% | n-propyl alcohol |
| 10% | acetic acid |
| 31% | water. |

This fuel had a heating value of 11,910 BTU/lb. (about 6.6 Kg-cal/g) and readily supported combustion.

It should be understood that the 65/35 ratio of Example II and the 50/50 ratio of this Example is the initial population ratio. The two species may multiply at different rates, and the ratio may change continually during the fermentation.

What is claimed is:

1. A method for producing a non-potable oxo- or oxy-aliphatic organic fuel boiling within the range of 20° to 200° C. and containing lower aliphatic monohydric alcohols or carbonyl compounds, which method comprises the steps of:
   (a) blending water, a cellulose- or hemicellulose-containing particulate mass, and a fermentation agent to form a fermentation medium, said fermentation agent being selected from the group consisting of:
   (i) a deliberate combination of at least two carbohydrase-producing Clostridium species in a ratio ranging from 9:1 to 1:9, at least one of said species being capable of producing cellulase; and
   (ii) the carbohydrase enzymes produced by said combination;
   (b) fermenting said particulate mass at fermentation temperatures, with supression of carboxylic acid production, until fermentation products are produced; and
   (c) recovering the non-potable organic fuel from said fermentation medium.

2. A method according to claim 1, wherein said combination is aerotolerant and comprises *Clostridium cellobioparum* and a second Clostridium species capable of producing an enzyme selected from the group consisting of cellobiase, glucosidase, glucase, and combinations thereof; at least 40% of the population of the Clostridia being the *Cellobioparum* species.

3. A method according to claim 2 wherein said second Clostridium species is *Clostridium acetobutylicum*.

4. A method according to claim 1 wherein said fermentation agent includes: (1) carbohydrase enzymes obtained from *Clostridium cellobioparum*, and (2) an enzyme selected from the group consisting of glucosidase, cellobiase, and combinations thereof; at least 40% of the total enzyme activity being the carbohydrase enzymes obtained from *Clostridium cellobioparum*.

5. A method according to claim 1 wherein said fermentation is carried out at 30°-45° C. and a pH of 3 to 7, with access to atmospheric oxygen.

6. A method according to claim 1 wherein said organic fuel, tested as an anhydrous blend of organic liquids, has a heat of combustion in excess of 4 Kg-cal/g, boils at 50°-140° C., and comprises organic liquids selected from the group consisting of lower alkanols, lower ketones, lower aldehydes, and mixtures thereof.

7. A method according to claim 6 wherein said organic fuel on an anhydrous basis, contains less than 5% by weight of acetic acid and is substantially free, except for trace amounts, of formic and butyric acids, the major amount of said fuel consisting essentially of $C_1$ to $C_4$ alkanols.

8. A method according to claim 1 wherein said particulate mass of said step (a) is sufficiently finely divided to pass a —50 U.S. mesh screen.

9. A method for producing a non-potable, liquid $C_1$ to $C_5$ oxo- or oxy-aliphatic fuel while suppressing the production of aliphatic carboxylic acids, said fuel boiling within the range of 50° to 150° C., which method comprises the steps of:
   (a) blending water, a cellulose- or hemicellulose-containing particulate mass which is generally —50 U.S. mesh in particle size, and a fermentation agent to form a fermentation medium, said fermentation agent being prepared by deliberately combining at least two enzyme systems including a major amount of enzyme system obtained from *Clostridium cellobioparum* and a minor amount, greater than 20% of enzyme system obtained from *Clostridium acetobutylicum*;
   (b) maintaining the said fermentation medium at normal ambient temperatures for at least about 12 hours;
   (c) fermenting the cellulose or hemicellulose in said fermentation medium for at least 12 hours at a fermentation temperature ranging from 5° to 50° C.

and a pH ranging from 5 to 7 until aliphatic carbonyl compounds or aliphatic monohydric alcohols are produced by said fermentation medium;

(d) separating said aliphatic carbonyl compounds or aliphatic monohydric alcohols from said fermentation medium.

10. A method according to claim 9 wherein said combination of enzymes is associated with live cellular material of *Clostridium cellobioparum* and *Clostridium acetobutylicum*, and said fermentation temperature is 30°–40° C.

11. A method according to claim 9 wherein said combination of enzymes is unassociated with live cellular material.

12. A method according to claim 10 wherein the population of Clostridia is 60–70% *Clostridium cellobioparum* organisms.

13. A method according to claim 11 wherein 60–70% of the carbohydrase enzyme activity is carbohydrase obtained from *Clostridium cellobioparum*.

* * * * *